(12) United States Patent
Peterson et al.

(10) Patent No.: US 10,495,592 B1
(45) Date of Patent: Dec. 3, 2019

(54) USE OF METAL-ORGANIC FRAMEWORKS AND METAL OXIDES FOR SENSING CHEMICALS USING ELECTRICAL IMPEDANCE SPECTROSCOPY

(71) Applicant: U.S. Army Edgewood Chemical Biological Center, APG, MD (US)

(72) Inventors: Gregory W Peterson, Belcamp, MD (US); Augustus W Fountain, III, Bel Air, MD (US); Jennifer R Soliz, Ellicott City, MD (US); Adam J Hauser, Tuscaloosa, AL (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 87 days.

(21) Appl. No.: 15/689,664

(22) Filed: Aug. 29, 2017

(51) Int. Cl.
*G01N 27/02* (2006.01)
*G01N 33/22* (2006.01)
*G01N 33/20* (2019.01)
*G01N 33/00* (2006.01)

(52) U.S. Cl.
CPC ....... *G01N 27/026* (2013.01); *G01N 33/0037* (2013.01); *G01N 33/227* (2013.01); *G01N 33/0042* (2013.01); *G01N 33/0052* (2013.01); *G01N 33/0054* (2013.01); *G01N 33/0057* (2013.01); *G01N 33/20* (2013.01)

(58) Field of Classification Search
CPC .... G01N 27/02; G01N 27/026; G01N 33/227; G01N 33/0037; G01N 33/0042; G01N 33/0052; G01N 33/0054; G01N 33/0057; G01N 33/20; Y10T 436/16; Y10T 436/163333; Y10T 436/17; Y10T 436/170769; Y10T 436/173076; Y10T 436/173845; Y10T 436/175383; Y10T 436/178459; Y10T 436/18; Y10T 436/186; Y10T 436/19; Y10T 436/25875

USPC .... 436/73, 75, 79, 81, 82, 83, 84, 106, 107, 436/110, 111, 113, 116, 117, 103, 104, 436/119, 122, 124, 149, 150, 151, 181; 422/82.01, 82.02
See application file for complete search history.

(56) References Cited

U.S. PATENT DOCUMENTS

| | | | | |
|---|---|---|---|---|
| 3,933,433 | A | * | 1/1976 | Hooker ................ G01N 27/122 436/134 |
| 9,770,703 | B1 | * | 9/2017 | Soliz .................. B01J 20/28009 |
| 2003/0217586 | A1 | * | 11/2003 | Gouma .................. G01N 27/12 73/31.06 |
| 2015/0020577 | A1 | * | 1/2015 | Luebke .................. G01N 27/12 73/31.06 |
| 2018/0195990 | A1 | * | 7/2018 | Yassine ................ G01N 27/125 |
| 2018/0231485 | A1 | * | 8/2018 | Potyrailo ............. G01N 27/125 |

FOREIGN PATENT DOCUMENTS

GB     2166247    *   4/1986

OTHER PUBLICATIONS

Peterson et al. Dalton Transactions, vol. 45, Oct. 2016, pp. 17113-17116 and Supplementary Information.*
Harris et al. Dalton Transactions, vol. 46, Jul. 2017, pp. 10791-10797.*

* cited by examiner

*Primary Examiner* — Maureen Wallenhorst
(74) *Attorney, Agent, or Firm* — Ulysses John Biffoni

(57) ABSTRACT

Provided are processes for the sensitive detection of the presence of, absence of, and optionally the identity of, one or more chemical agents. The processes use the binding of chemical agents to a metal organic framework or metal oxide/hydroxide electrically connected to a pair of electrodes to detect low levels of chemical in a sample. By exposing the surface of the metal organic framework or the surface of the metal oxide/hydroxide to the chemicals and then measuring changes in impedance magnitude and/or phase shift through electrical impedance spectroscopy, the presence of a chemical agent is readily detected.

22 Claims, 12 Drawing Sheets

US 10,495,592 B1

USE OF METAL-ORGANIC FRAMEWORKS AND METAL OXIDES FOR SENSING CHEMICALS USING ELECTRICAL IMPEDANCE SPECTROSCOPY

U.S. GOVERNMENT INTEREST

The invention described herein may be manufactured, used and/or licensed by or for the U.S. Government.

FIELD

This invention relates generally to detection of molecules in a gaseous or liquid environment. More particularly, the invention relates to detection of explosives or toxic chemicals.

BACKGROUND

Detection of explosives or toxic chemicals remains an essential pan of protecting both military and civilian personnel both in the field and in controlled environments. With increased exposure to threats from improvised explosive devices and other homemade explosives, detection of trace amounts of explosive material in the field is essential. Current deployable explosive and toxic chemical sensing methods utilize ion mobility mass spectrometry, gas chromatograph mass spectrometry, X-ray imaging, Raman spectroscopy, and other such complex techniques. While these techniques are highly selective, each method has its own shortcomings, such as low resolution, competing ion, or molecule side reactions, response variation from different compositions of analytes, limited response range, and time-consumption. in addition, most of these techniques require bulky equipment and require significant training for proper utilization.

Despite remarkable improvements in detector technology, spectroscopic detection is still bulky and expensive, and requires significant training for interpretation of results, particularly in a many-analyte field environment, and colorimetric system field interpretation is subjective, and results are difficult to store for later review. More importantly, current colorimetric systems have no mechanism for determination of unknown chemicals that may also react with the detection material. As such, there is a need for improved materials, methods and devices for detection of analytes such as explosive materials in the field.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Provided are unique processes for the detection and optional identification of one or more chemical on pounds in or on a sample. The processes capitalize on the use of electrical impedance spectroscopy for the sensitive and highly selective chemical compound detection. Utilizing one or more detection agents such as a metal organic framework, metal oxide, or combinations thereof, that selectively and robustly bind to the target chemical compounds, powerful and fingerprint specific detection of chemical compounds or agents is achieved. In some aspects a process includes: adsorbing a chemical on a surface comprising one or more detection agents, the one or more detection agents comprising a metal organic framework, metal oxide, or both, the surface intermediate to and electrically connected to a pair of electrodes; and detecting the presence of the chemical by subjecting the surface to electrical impedance spectroscopy. It is appreciated that in some aspects the surface may further include a polymer, an absorbent, or combination thereof. The step of detecting optionally includes subjecting the surface to an alternating current at a range of frequencies, the range from $10^{-2}$ to $10^6$ Hertz, subjecting the surface to an applied voltage of 10 milliVolts to 10 Volts, or combinations thereof. Optionally, the material is subjected to an alternating current or a direct current for detection of one or more chemical agents. Optionally, the detection agent is or includes a porous media. Optionally, the detection agent is a metal organic framework that includes at least one pendant group in the framework, the pendant group comprising an amine, nitro, or halide. A detection agent may include a metal, wherein the metal is, selected from the group consisting of: Al; Si; Cr: Fe; Co; Ni; Cu; Zn; Mn; Ti; V; Zr; Ca; Mg; and the lanthanides. Optionally, the metal organic framework is a UiO metal organic framework. Optionally, the metal organic framework is selected from the group consisting of NU1000, UiO-66, UiO-66-NH2, UiO-67, $Zn_2(bpdc)_2(bpee)$, PCN-250, MIL-53-$NH_2$, MIL-125-$NH_2$, ZIF-8, PCN-250, MOF-74 (M-DOBDC), and PCN-222. In some aspects the detection agent comprises a metal oxyhydroxide. The metal oxyhydroxide optionally includes a transition metal or cation. Optionally, the metal oxyhydroxide comprises a metal selected from the group consisting of: Al; Si; Cr; Fe; Co; Ni; Cu; Zn; Hf; Mn; Ti; V; Zr; Ca; Mg; and the lanthanides. In some aspects of the process, the impedance results are reversible after the interdigitated capacitor comprising the material of interest has been exposed to the analyte following exposure to air for 3 days. Optionally, the interdigitated capacitor comprising the material of interest is reusable after chemical exposure. The surface used fur detection optionally includes a polymer exhibiting dielectric properties, optionally polyvinylidene fluoride.

Also provided are processes for detecting the presence of a chemical including: adsorbing a toxic chemical or an explosive chemical to a dielectric surface comprising one or more detection agents comprising a metal organic framework, a metal oxide/hydroxide, or combination thereof; and detecting the presence of the chemical by subjecting the material to electrical impedance spectroscopy. In such processes the detection agent optionally includes a metal organic framework selected from the group consisting of NU1000, UiO-66, UiO-66-$NH_2$, UiO-67, $Zn_2(bpdc)_2(bpee)$, PCN-250, MIL-53-$NH_2$, MIL-125-$NH_2$, ZIF-8, PCN-250, MOF-74 (M-DOBDC), and PCN-222. In other aspects, the detection agent includes zirconium oxyhydroxide, iron oxide, or any transition metal oxide/hydroxide. Optionally, the toxic chemical includes nitrogen dioxide, sulfur dioxide, chlorine, ammonia, and organophosphates. Optionally, the explosive chemical composes ammonium nitrate, cyclotrimethylenetrinitramine (RDX), pentaerythritol tetranitrate, octogen (HMX), trinitrotoluene, 2,4-dinitrotoluene, or 2,6-dinitrotoluene.

The processes as provided herein readily achieved fingerprint and highly sensitive detection of chemical agents that can be readily employed in the field.

DETAILED DESCRIPTION

Figure 1A:
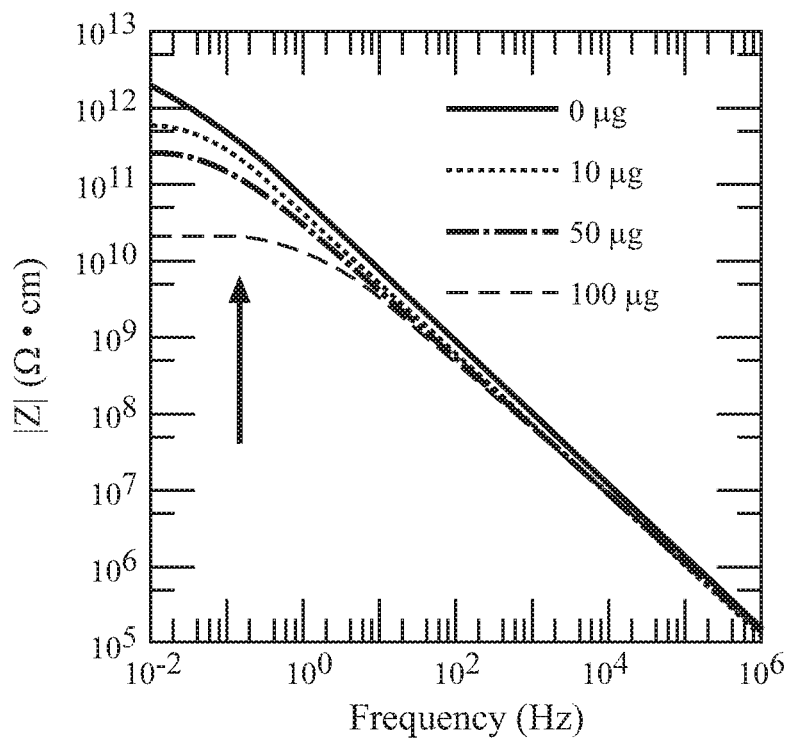
FIG. 1A illustrates frequency dependent impedance magnitude of UiO-66-$NH_2$ exposed to various concentrations of 2,6-DNT.

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise.

"Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Provided herein are methods for the detection of one or more chemicals that have excellent sensitivity and selectivity as well as being capable of deployment outside a laboratory setting such as in the field. The processes utilize electrical impedance spectroscopy (EIS) in conjunction with metal oxides (herein MOs) or metal-organic frameworks (herein MOFs) to detect the presence or absence of the chemicals, optionally chemicals that have characteristics of explosives or explosive simulants. Due to the porous nature of examples of these materials, especially of MOFs, but also of MOs, these detection agents are able to sorb chemicals and in some aspects selectively absorb chemicals. In some aspects, the reactive groups or backbone of the MOFs or MOs interact with the chemicals such as by ionic or hydrogen bonding interactions. The MOF, MO, and potential combination with polymeric materials may result in dielectric materials that have inherent capacitance. Interacting one or more target chemicals with such dielectric materials produces a change in capacitance, resulting in changes to impedance magnitude and phase angle, EIS is able to detect changes to the dielectric material at very low concentrations, resulting in trace detection capabilities.

The novel processes described herein involve employing electrical impedance spectroscopy (EIS) for the detection of one or more chemicals from a sample. Such processes include contacting a chemical with one or more detection agents, optionally on a surface, whereby the detection agent is suitable for use in EIS. A detection agent is positioned intermediate to a pair of electrodes and electrically connected to the pair of electrodes. The system is robust and able to detect a variety of chemicals through specific interactions between the chemical and the detection agent(s). As such, a detection agent functions to interact with a chemical thereby altering one or more characteristics of the surface upon which the detection agent is absorbed.

A wide variety of chemicals may be detected by the processes of this disclosure. In some aspects, a chemical includes one or more terminal reactive groups suitable for interacting with a MOF or MO on a surface. A terminal reactive group is optionally a nitro, amine, halide, or other suitable reactive group. The term "terminal" as used herein means that the reactive group forms or is a portion of a chemical such that it is free to react with an MOF or MO optionally to thereby absorb the chemical thereto. The reactive group may be at the terminus of a linear molecule, or may be intermediate at any location within the chemical.

A chemical is optionally a toxic chemical. In some aspects, a toxic chemical encompasses chemical warfare agents (CWAs), including but not limited to toxic organophosphorus-type agents, mustard, gas and derivatives, and similar such art-known toxins. Illustrative specific examples of CWAs include but are not limited to bis-(2-chloroethyl) sulfide (HD or mustard gas), pinacolyl methylphosphonofluoridate (GD), Tabun (GA), Sarin (GB), cyclosarin (GF), and O-ethyl S-(2-diisopropylamino)ethyl methylphosphonothioa (VX), other toxic organophosphorus-type agents, their analogs or derivatives, and similar such art-known toxins. In addition, unless otherwise stated, the term "toxic chemical" as used herein is also intended to include toxic industrial chemicals, including, but not limited to, organophosphorus-type insecticides, and, the like. Mineral acids, such as for example ammonia ($NH_3$), methyl amine ($CH_3NH_2$), HCl, HF, HBr, $SO_3$, $SO_2$, $HNO_3$, $H_2S$, or combinations thereof etc. are also exemplary toxic chemicals.

Optionally, a chemical is an explosive chemical. Many explosives have amino functionality adjacent to nitro functional groups, which serve as electron withdrawing groups. As the number of nitro groups increase, the greater the ability for the displacement with nucleophiles. Explosive chemicals as illustrated herein are optionally characterized by a laser shock velocity of 650 m/s or greater under the conditions of Gottfried, J L, *Phys. Chem. Chem. Phys.*, 2014, 16, 21452. Illustrative examples of an explosive chemical include but are not limited to: ammonium nitrate ($NH_4NO_3$), 2,4-dinitrotoluene, 2,6-dinitrotoluene, 1,3,5-trinitro-1,3,5-triazacyclohexane (1,3,5-trinitroperhydro-1,3,5-triazine; RDX); 1,3,5,7-tetranitro-1,3,5,7-tetrazocane (1,3,5,7-tetranitro-1,3,5,7-tetrazocane; HMX); 2,2-bis (hydroxymethyl)1,3-propanediol (pentaerythritol tetranitrate; PETN); 2,4,6-trinitrotoluene (2-methyl-1,3,5-trinitrobenzene; TNT), 1,2,3-trinitroxypropane (trinitroglycerin; TNG), 2,3-dimethyl-2,3,-dinitrobutane (2,3-dimethyl-2,3-dinitrobutane; DMDNB); triacetone triperoxide (TATP); hexamethylene triperoxide diamine (HMTD); other peroxide or nitrate based explosive materials; gunpowder(s); pentaerythritol (2,2-Bis(hydroxymethyl)1,3-propanediol; PE); military or commercial grades of C4; Semtex A1; Semtex H; 2,4-dinitroanisole (DNAN), 1,3-Dinitrobenzene (1,3-DNB); 1,3,5-trinitrobenzene (1,3,5-TNB); hexanitrostilbene (HNS); croconic acid; pentolite; 2,4,6-triamino-1,3,5-trinitrobenzene (TATB); comp B; nitrotriazalone (NTO); hexanitrohexaazaisowurtzitane (CL-20); 1,1-diamino-2,2-dinitroethene (DADNE; FOX-7); or combinations thereof.

In the processes as provided herein a chemical is contacted to, optionally absorbed to, a surface that includes one or more detection agents. A detection agent is an agent suitable for sorbing, optionally absorbing a chemical. A surface includes at least one detection agent. A surface optionally includes 2 or more detection agents. A surface optionally includes 2, 3, 4, 5, 6, or more detection agents. A detection agent is optionally a metal organic framework or a metal oxide. Due to the porous nature of MOFs and MOs, these materials are able to adsorb chemicals thereby localizing and optionally concentrating the chemical from a sample. Furthermore, the reactive groups on MOB and MOs are able to interact with explosives and explosive simulants. The MOF and MO are suitable for incorporation into dielectric materials that have inherent capacitance. Through these interactions, changes in capacitance in the surface may be observed as well as the resulting changes to impedance magnitude and phase angle. EIS is able to detect changes to the dielectric, material at very low concentrations, resulting in trace detection capabilities.

A detection agent is optionally a metal oxide. Metal oxides (MOs) are ceramic materials composed of cations coordinated with oxygen ligands. For the purposes of this disclosure, MOs consist of crystalline materials as well as amorphous materials; therefore including hydroxides and oxyhydroxides. A metal oxide includes a metal. A metal is optionally Al, Si, Cr, Fe, Co, Ni, Cu, Zn, Hf, Mn, Ti, V, Zr, Ca, Mg, the lanthanides, or combinations thereof. One exemplary metal oxide is zirconium hydroxide ($Zr(OH)_4$). Zirconium hydroxide is a known nucleophile and reacts with explosives by displacing the nitro groups; therefore, this material is of specific interest for explosives detection, or detection of other chemicals that include one or more nitro groups. Zirconium hydroxide or other metal oxides may be prepared by precipitating a metal salt, optionally zirconium salt, such as for example metal oxynitrate and metal oxychloride, in aqueous solutions using alkaline solutions such as lithium hydroxide, sodium hydroxide and potassium hydroxide. The alkaline solutions can be used to increase the pH of the solution, thereby bringing about the formation of the porous metal hydroxide via precipitation. Other bases, such as ammonium hydroxide, cats also be used.

Such processes optionally produce a porous metal hydroxide that is substantially pure. The term "substantially pure" is meant free of additional contaminating metals, salts, acids, or other materials that may detract from the effectiveness of the resulting porous metal hydroxide. Substantially pure optionally means 90% pure, optionally 91% pure, optionally 92% pure, optionally 93% pure, optionally 94% pure, optionally 95% pure, optionally 96% pure, optionally 97% pure, optionally 98% pure, optionally 99% pure, optionally 99.1% pure, optionally 99.2% pure, optionally 99.3% pure, optionally 99.4% pure, optionally 99.5% pure, optionally 99.6% pure, optionally 99.7% pure, optionally 99.8% pure, optionally 99.9% pure, or of greater purity.

Porous metal hydroxide optionally has a porosity representing a surface area of at least 100 $m^2/g$, optionally greater than 250 $m^2/g$. In some aspects, a surface area is from 100 $m^2/g$ to 600 $m^2/g$, or any value or range therebetween, optionally 250 $m^2/g$ to 600 $m^2/g$, optionally 100 $m^2/g$ to 450 $m^2/g$, optionally 250 $m^2/g$ to 450 $m^2/g$.

Pore volume of a porous metal hydroxide is optionally at or greater than 0.1 $cm^3/g$, optionally at or greater than 0.3 $cm^3/g$. In some aspects, pore volume is 0.1 $cm^3/g$ to 1.2 $cm^3/g$, or any value or range therebetween, optionally 0.3 $cm^3/g$ to 1.2 $cm^3/g$, optionally 0.1 $cm^3/g$ to 0.9 $cm^3/g$ optionally 0.3 to 0.9 $cm^3/g$.

Alternatively, zirconium hydroxide may be purchased as a commercial product from vendors that include Magnesium Electron (Flemington, N.J., USA). The structure of metal hydroxide, e.g., $Zr(OH)_4$, may be represented as a two-dimensional square lattice, each connected by a double hydroxyl bridge yielding a stoichiometric $Zr(OH)_4$, $Zr(OH)_4$ particles contain both terminal and bridging hydroxyl groups (Southern et al., *Chem. Mater* 14 (2002) 4313; DeCoste et al., *Langmuir* 27 (2011) 9458).

In some aspects, a detection agent includes a MOF. MOFs are reticular porous structures formed through the bonding (covalent or otherwise) of metal oxide (or other) secondary building units (SBUs) and organic linkers. Both the SBU and organic linker can be tuned by changing metal type, functional group, and size, resulting in a wide potential range of frameworks with varying functionality and porosity (surface area, pore volume, pore aperture). UiO-66-$NH_2$ (shown in FIG. 2b) is one of many MOFs of as used in the processes provided herein. Specifically, the electron donating functional group in UiO-66-$NH_2$ interacts with structures containing nitro groups, and is therefore of particular interest for explosives detection. Since the surface area (1182 $m^2$/g) of UiO-66-$NH_2$ is high, there is a greater amount of reactivity with such explosives.

The processes as provided herein are optionally not limited to the use of UiO-66-$NH_2$. Due to the ability to change/tune both the SBU (e.g., changing metal type) and organic linker (e.g., putting functional groups on the linker, using larger/bulkier/longer linkers), the formation of several type of MOF structures is possible. There are multiple sub-groups of MOFs, such as isoreticular MOFs (IRMOFs), materials from institute Lavoisier (MIL) MOFs, zeolitic imidazolate frameworks (ZIFs), and others. Typically these groups are based on similarities of the structures. For example, most of the IRMOFs contain zinc acetate SBUs, and changing the linker results in a wide range of porous structures. UiO-66, as one example, utilizes a terephthalic acid (aka benzene dicarboxylate) linker that can be functionalized with a variety of groups, such as an amine group (herein known as UiO-66-$NH_2$), MIL MOFs, although typically utilizing different metals such as iron, chromium, and aluminum, can also be functionalized with amine groups. As such, an MOF as used for the detection of a chemical as provided herein is optionally an amine containing MOF whereby the amine is present in the MOF as a functional group capable of reacting with a chemical.

Optionally, a MOF is a UiO-66 analog such as UiO-66-$NH_2$. UiO-66 MOFs are formed of $Zr_6O_4(OH)_4$ octahedra that are 12-fold connected to adjacent octahedra through a 1,4-benzene-dicarboxylate (BDC) linker, resulting in a highly packed fcc structure. Methods of forming such MOFs including amine-containing MOFs are illustratively presented in *J. Am. Chem. Soc.*, 130, 13850 (2008), *Chem. Commun.* 46, 7700 (2010), and U.S. Pat. No, 9,175,025 B2. In some aspects, an MOF is a Zn(DABCO) MOF or PCN-250. These and other operable MOFs as well as illustrative methods of synthesis of such MOB may be found in Stock and Biswas, *Chem. Rev.*, 2012; 112 (2):933-969 and Feng, D. et al., Nat. Commun. 5:5723 doi: 10.1038/ncomms6723 (2014).

While MOFs used in several aspects, include amine-containing MOFs. Other MOFs may be used as well as long as the MOF is capable of sorbing, optionally absorbing a chemical. Other illustrative examples of MOFs include but are not limited to NU1000, UiO-66, UiO-66-NH2, UiO-66 analogs; UiO-67, $Zn_2(bpdc)_2$(bpee), PCN-250, MIL-53-$NH_2$, MIL-125-NH2, ZIF-8, PCN-250, MOF-74 (M-DOBDC), and PCN-222.

A MOF includes a metal. A metal is optionally: Al; Si; Cr; Fe; Co; Ni; Cu; Zn; Hf; Mn; Ti; V; Zr; Ca; Mg; or a lanthanide. Optionally, a metal is selected from the group of Al, Cr, Fe, Hf, Mn, Ti, V, Zr, Ca and Mg. In some aspects, a metal is Zr or Ti. Optionally, a metal is Zr.

A MOF has a porous structure. Pore volume (optionally average pore volume) of an MOF is optionally at or greater than 0.1 cubic centimeters per gram ($cm^3$/g), optionally at or greater than 0.3 $cm^3$/g. In some aspects, pore volume is 0.1 $cm^3$/g to 1.2 $cm^3$/g, or any value or range therebetween, optionally 0.3 $cm^3$/g to 1.2 $cm^3$/g, optionally 0.1 $cm^3$/g to 0.9 $cm^3$/g, optionally 0.3 $cm^3$/g to 0.9 $cm^3$/g.

An MOF has a surface area. Increased surface area correlates with improved separation capability and reactability of the MOF used in a filtration media. Surface areas of exemplary MOFs as measured using the Brunauer Emmett Teller (BET) technique are optionally in excess of 600 square meters per gram ($m^2$/g). In some aspects, a surface area is at or in excess of 700 $m^2$/g, optionally 800 $m^2$/g, optionally 900 $m^2$/g, optionally 1000 $m^2$/g, optionally 1100 $m^2$/g, optionally 1200 $m^2$/g, optionally 1100 $m^2$/g, optionally 1400 $m^2$/g, optionally 1500 $m^2$/g, optionally 2000 $m^2$/g, optionally 3000 $m^2$/g, optionally 4000 $m^2$/g, optionally 5000 $m^2$/g. In some aspects, the BET surface area of a MOF is between 800 $m^2$/g and 1100 $m^2$/g.

In the processes as provided herein, a detection agent acts as a surface or contacts a surface directly or via a linker. A surface is electrically connected to a pair of electrodes. A surface optionally includes or is formed of a detection agent or includes a detection agent, optionally along with a polymer, binder, or other additive. In some aspects, a surface is a structure that may be placed between two electrodes such as in the form of a parallel plate capacitor. As an illustrative example, a powder detection agent is optionally combined with a binder, polymer, other additive, or combinations thereof and optionally pressed into the form of a pellet. Prior to or following pelleting, the detection agent may be contacted with a sample that may or may not include a chemical, wherein the step of contacting is for a suitable time to allow interaction of the chemical with the detection agent. Following contact, the pelleted detection agent is placed within a parallel plate capacitor which is then subjected to a current of desired characteristics to allow the detection of the presence or absence of a chemical in the sample.

Optionally, a detection agent is contacted to or disposed on a surface. A surface is optionally formed of one or more dielectric materials. The dielectric constant (the relative permittivity of the dielectric media) and associated dielectric loss inform the characteristics of a capacitive device. Measuring the dielectric response upon exposure can be employed by alternating current (AC) impedance spectroscopy, wherein sorption of one or more chemicals to a detection agent results in frequency-dependent changes to the impedance amplitude and, phase. Coupling these changes allows selectivity for a wide variety of compounds. Because the dielectric constant of a material can change differently in response to different chemical interactions, this approach offers specificity. Furthermore, integrating dielectrics into chemical sensors offers portability, tunability, simplicity, low costs. and rapid response times than currently in-place systems. The complex impedance (Z=R+iX of a dielectric material, where R and X are the measured resistance and reactance) can exhibit analyte/quantity-dependent shifts due to adsorption/interaction with various species. By providing sites targeting specific. molecules, sorption can be further tuned for signal strength or specificity.

A dielectric material used in a surface is any suitable material to which a detection agent as provided herein may be successfully associated with. A dielectric material may be a ceramic, mica, glass, or a dielectric polymer. In some aspects, a dielectric material is polymer. A dielectric polymer is optionally a fluoropolymer or an aromatic-containing polymer. Optionally, a dielectric material is polyvinylidene fluoride (PVdF), methylsilsesquioxane, polyarelene ether, polyethylene, polystyrene, or a polyimide. Other illustrative polymers include but are not limited to polyethyleneimine (PEI) and poly(vinylpyrrolidinone) VP).

Alternatively, a detection agent may be in the form of a surface such as a thin film. Illustrative examples of such films include nano-fiber kebab structures such as those exemplified by Zhao et al., *Angew. Chem. Int. Ed.* 2016; 55:13224-13228. Such nano-fiber kebab structures are optionally used by laying the fibers between a parallel plate on a parallel plate capacitor or connected directly to electrode leads.

In other aspects, a surface is a portion of an interdigitated capacitor (IDC). It is recognized in the art that the terms "interdigitated electrode" and "interdigitated capacitor" are both directed to the same device and are therefore used interchangeably. The term interdigitated capacitor (IDC) and interdigitated electrode (IDE) are, therefore, used interchangeably in this disclosure. The potential advantage of this approach is that (in-situ) analysis of the impedance at one or many frequencies provides an immediate frequency-dependent "shift fingerprint" that cats be interpreted quickly and easily for many different analytes or several in the same environment. One or more detection agents, optionally combined with a polymer, binder, or other additive may be applied to the surface of an IDC by techniques recognized in the art such as ultra-sonic spray deposition or other technique.

A detection agent is contacted with a sample that may or may not contain one or more chemicals. A sample may be a liquid, solid, or gas. Contacting is optionally by any suitable method such as immersion, incubation, rubbing, blowing, or other method by which a chemical may come into contact with a detection agent. A sample is optionally a liquid sample. A sample is optionally a gaseous sample. A detection agent, optionally in the form of a pellet, powder, film, or present on a surface such as the surface of an interdigitated electrode device is optionally immersed in a liquid or gaseous sample for a suitable contact time. Following the contact time, or during the contact time, the surface or other form of detection agent is subjected to current for EIS detection of the presence or absence of the chemical bound to the surface.

As an illustrative example, a detection agent in the form of a powder may be immersed in a liquid sample that includes one, or more chemicals therein. After a suitable contact time. optionally 1 minute to 48 hours, the liquid may be evaporated or the detection agent otherwise isolated from the liquid, The detection agent may then be pelleted such as through the use of a Carver press and placed between a pair of electrodes in a parallel plate sample holder which may then be analyzed by EIS for the presence or absence of chemical bound to the detection agent. Illustrative processes of EIS analysis are provided in Peterson, et al., *Dalton Trans.*, 2016; 45:17113-17116.

In another example, an IDE with a detection agent hound thereto is used to detect one or more chemicals. An IDE with one or more detection agents bound thereto may be immersed in a sample solution containing chemical for detection, such that the chemical will be contacted by the detection agent. An electric circuit through the interdigitated electrodes induces an electric field between the interdigitated electrodes. The bound chemical causes a detectable change in the impedance in the electric field between the electrodes. The total impedance consists of a transient component (inductance and capacitance) and a non-transient component (resistance). As the signal frequency increases, the transient impedance decreases causing the impedance to be resistive between the electrodes. Different concentrations of chemical yield different changes in impedance between the electrodes. Also, different chemical types can induce different changes in impedance over the frequency range. Therefore, the IDE or other device can detect and distinguish between multiple chemical agents present in a sample based upon the impedance produced over the frequency range.

In an example of the manufacture of an IDE sensor, the sensor may be fabricated by depositing an ultra-thin layer of metal onto the surface of a silicon chip to form an interdigitated electrode array and then covalently binding detection agent optionally specific for a particular chemical onto the silicon surface between the interdigitated electrodes. The sensor may then be mounted t. n a support such as an elongated probe or handle enabling the sensor to be immersed into or otherwise contacted with a sample. Detection of a chemical may be performed by immersing the sensor into a sample for a time sufficient for the detection agent to bind the chemical to be detected, optionally removing the sensor from the sample, optionally immersing the sensor into an aqueous neutral solution, and measuring the change in impedance wherein an increase in impedance indicates that the sample contains the chemical.

A process includes detecting the presence or absence of a chemical in a sample by subjecting the surface to EIS. EIS is optionally performed by subjecting a detection agent with a chemical bound thereto to an electric field with a varying frequency range. The frequency range may be selected based on the chemical to be detected. In some aspects, a frequency range is from $10^{-2}$ to $10^6$ Hz or any value or range therebetween. For some chemical agent such as 2,6-DNT, for example, this frequency range will provide a fingerprint response for both impedance (real and imaginary), phase angle, capacitance. etc. allowing for detection and identification of chemical. Optionally, specific narrower frequency ranges or discrete frequencies can be used to shorten the analysis time and determine the same parameters for identification or detection of a chemical bound to the detection agent. In some aspects, a frequency range is 10 to 0.01 Hz, optionally 0.01 to 1 Hz, optionally 1 to 10000 Hz.

A process optionally includes subjecting a detection agent to EIS using one or more voltages applied to the detection agent. A detection agent is optionally subjected to a voltage from 10 millivolts (mV) to 12000 mV, or any value or range therebetween. Optionally, a detection agent is subjected to voltages from 10 mV to 1000 mV.

A process includes contacting a detection agent with a sample including one or more chemicals for a detection time. A detection time is optionally any time from 1 second to 48 hours or any value or range therebetween. Optionally, a detection time is a time suitable to subject the detection agent to one or more frequencies of alternating current. Optionally, a contact time is that suitable to evaporate a liquid in which a chemical is contained. In some aspects a detection time is 1 second to 24 hours, optionally 1 second to 1 hour, optionally 1 second to 1 minute.

The provided processes are uniquely suited to field ready systems for the detection of one or more chemical agents of interest. The processes may be readily achieved without the need for large equipment and can be performed sufficiently rapidly that use in a first response situation is possible.

Various aspects of the present disclosure are illustrated by the following not limiting examples. The examples are for illustrative purposes and are not a limitation on any practice of the present invention. It will be understood that variations and modifications can be made without departing from the spirit and scope of the invention.

EXPERIMENTAL

Example 1

Synthesis of UiO-66-NH$_2$

UiO-66-NH$_2$ was synthesized by Lawrence Berkeley National Laboratory. A microwave synthesis of the MOF UiO-66-NH$_2$ was prepared using zirconium tetrachloride, 2-aminoterephthalic acid, water and dimethylformamide. The metal salt was purchased from Alfa Aesar. Additional chemicals were purchased from Sigma Aldrich. The molar composition of the reaction, is 1 Zr$^{4+}$: 1 2-ATA: 3.17 H$_2$O: 297 DMF.

400 mL of DMF and 2 mL of DI H$_2$O were added slowly to 8.12 g of ZnCl$_4$ in an Erlenmeyer flask (gases are produced upon addition of solvent). In a separate Erlenmeyer flask 400 mL of DMF was added to 6.275 g of 2-aminoterephthalic acid. Both mixtures were stirred until completely dissolved. The solutions were then mixed together and heated by microwave irradiation in sealed vessels at 1500 W for 9 hr at 120° C. The resulting pale yellow powder was filtered and extracted with methanol in a Soxhlet extractor, after which the material was dried in air and then heated in an oven at 65° C. The material was subsequently activated in vacuum at 150° C. for 16 hours.

Example 2

Detection of 2,6-DNT Using UiO-66-NH$_2$

The UiO-66-NH$_2$ made as above is used for the detection of 2,6-DNT from a liquid sample. Briefly, 2,6-DNT at amounts of 10-100 µg/cm$^2$ powder (based on the eventual surface area of the cylindrical MOF pellet) was dissolved in approximately 5 mL of ethanol in a scintillation vial and stirred. To the solution, 500 mg of UiO-66-NH$_2$ was added. The mixture remained uncapped and the ethanol was allowed to evaporate over the course of a day. After evaporation, the remaining detection agent powder was pressed into 25 mm diameter pellets using a Carver press at 10,000 psi. Impedance measurements were collected on all materials using a Solartron Analytical 1260 equipped with a dielectric interface 1296 and sample holder 12962 with brass plates. Voltages ranging from 10 mV to 1V and frequencies ranging from 10$^{-2}$ to 10$^6$ Hz were used for EIS measurements.

Figure 1B:
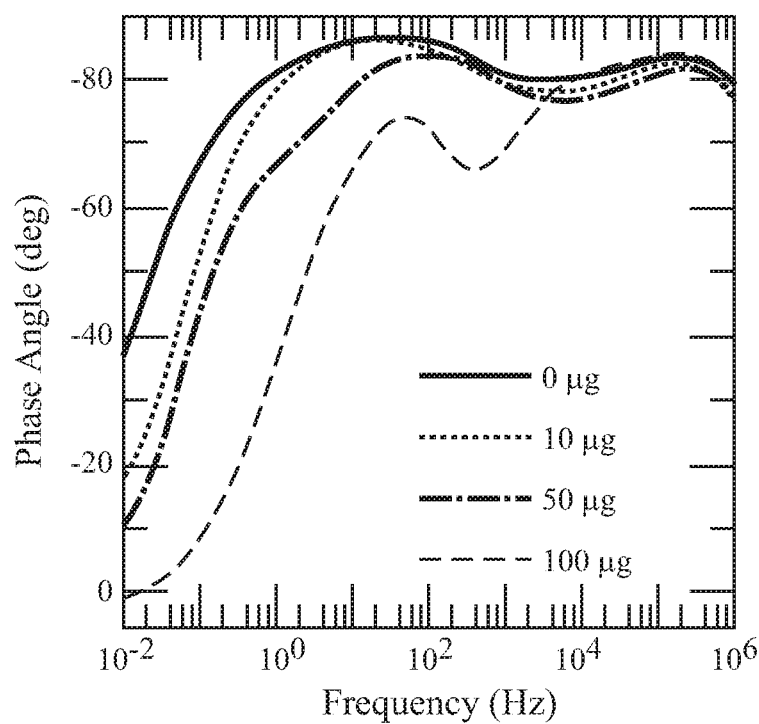
FIG. 1B illustrates frequency dependent phase angle of UiO-66-NH$_2$ exposed to various concentrations of 2,6-DNT.
Figure 2:
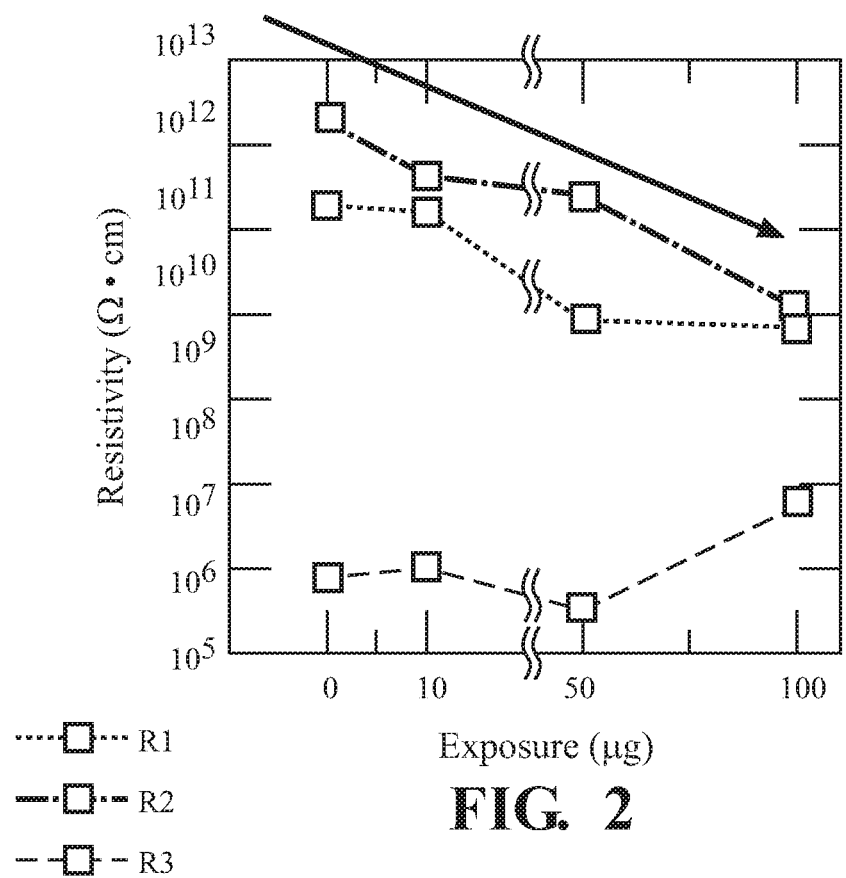
FIG. 2 illustrates resistivity as a function of exposure of UiO-66-NH$_2$ 2,6-DNT.

FIG. 1 illustrates the, use of UiO-66-NH$_2$ for sensing 2,6-DNT. Both the magnitude |Z| (FIG. 1A) and phase angle (FIG. 1B) as a function of frequency show changes in electrical response as UiO-66-NH$_2$ is exposed to various concentrations of 2,6-DNT. The |Z| changes by a couple of orders of magnitude in the low frequency regime. Changes at the higher frequency regime appear to be negligible as no significant changes occurred. As illustrated in FIG. 2. changes in the resistive behavior are reflected in the phase angle for UiO-66-NH$_2$, attributing to the changes from the conductive pathways within the pellet. The resistivity plot shows how the grain interior (R1), grain boundaries (R2), and ionic diffusion (R3) effects are impacted across the various concentrations of 2,6-dinitrotoluene exposures.

Example 3

Detection of NO$_2$ Using Zr(OH)$_4$

Zirconium hydroxide powder was obtained from MEL chemicals. The powder was formed into pellets at approximately 5000 psi and then forwarded for exposure to NO$_2$ vapor.

Figure 3A:
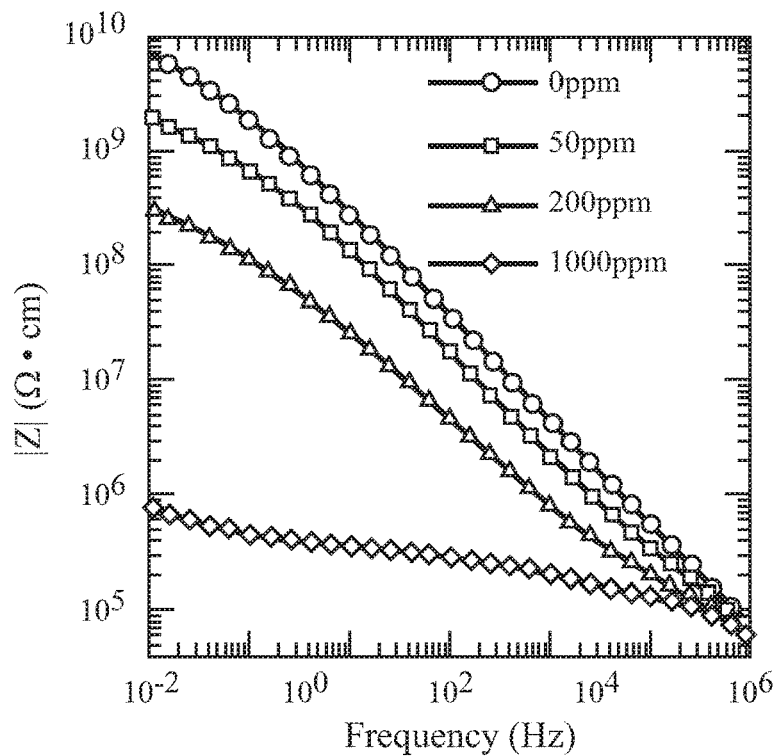
FIG. 3A illustrates changes in |Z| by binding of NO$_2$ by the detection agent Zr(OH)$_4$.

Zr(OH)$_4$ was exposed to 50, 200, and 1000 ppm of NO$_2$. From these exposures, significant changes in (FIG. 3A) and phase angle (FIG. 3C) were observed, leading to an increase in resistive behavior. Phase angle was measured using a parallel capacitor device with applied voltage V=0.1 V.

Figure 3B:
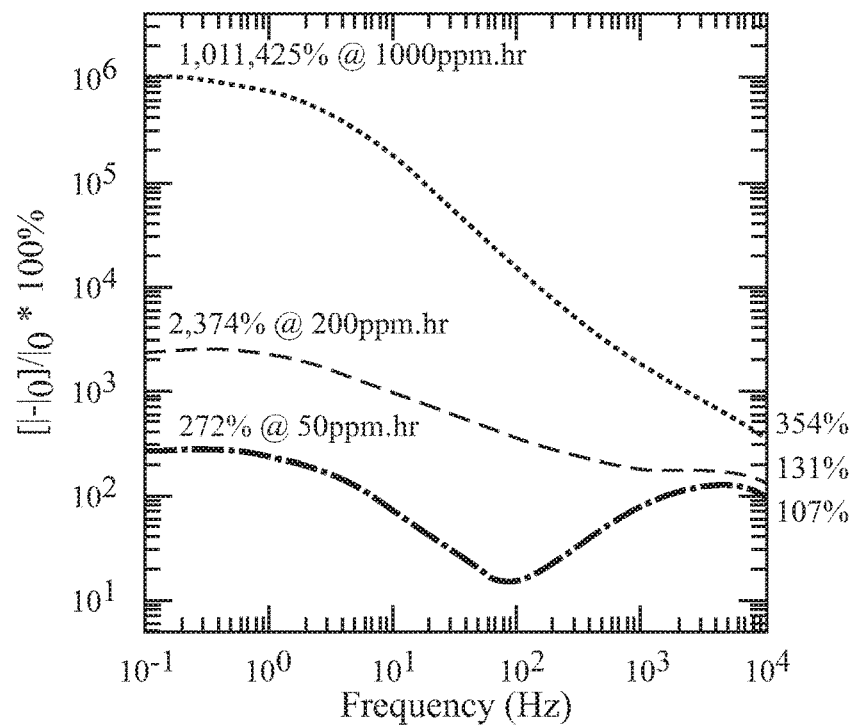
FIG. 3B illustrates percent current changes due to the binding of NO$_2$ by the detection agent Zr(OH)$_4$.
Figure 3C:
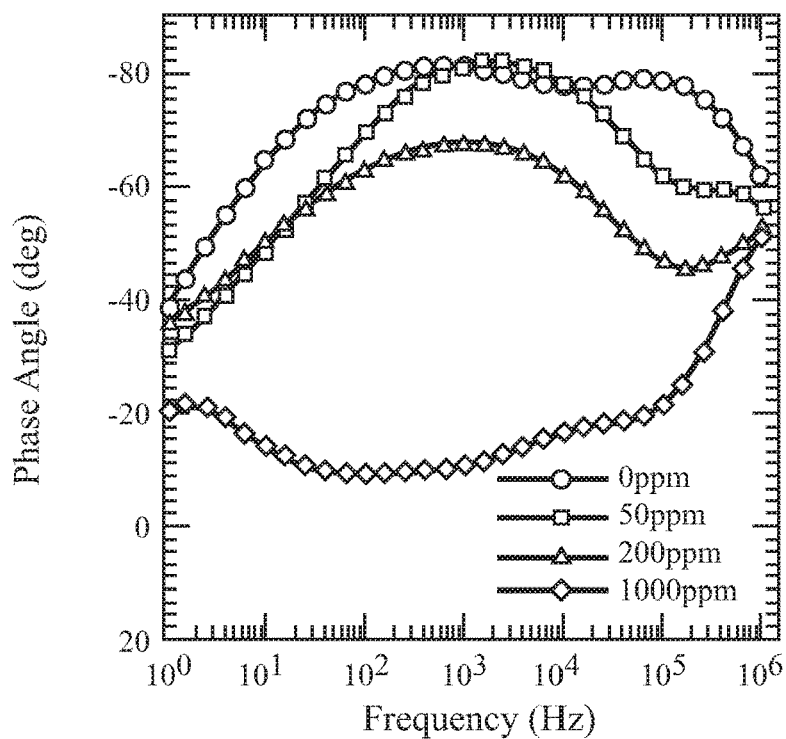
FIG. 3C illustrates changes in the resistive behavior as reflected in the phase angle due to the binding of NO$_2$ by the detection agent Zr(OH)$_4$.
Figure 3D:
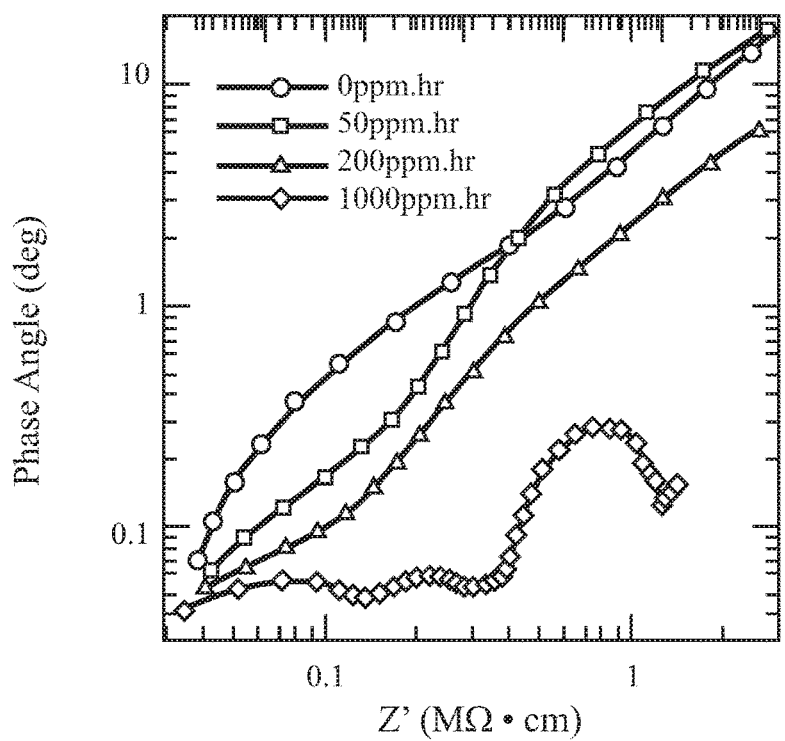
FIG. 3D illustrates impact of the Zr(OH)$_4$ grain interior, grain boundaries, and ionic diffusion from NO$_2$ exposures.

Across the frequency range, changes of 107% to 272%, 131% to 2374% and 354% to 1011425% in current were calculated from 50 ppm, 200 ppm, and 1000 ppm dosages, respectively, illustrating significant sensitivity due to the Zr(OH)$_4$ detection agent (FIG. 3B). The log-log Nyquist plot following exposures of Zr(OH)$_4$ pellets to 0 (grey circle), 50 (red circle), 200 (green circle), and 1000 (blue circle) ppm·hr NO$_2$ (FIG. 3D) shows the impact of how the grain interior (highest frequency regime), grain boundaries (next to highest frequency regime), and ionic diffusion (lowest frequency regime) effects were effected from NO$_2$ exposures.

Example 4

Detection of 2,6-DNT Using Zr(OH)$_4$

Figure 4A:
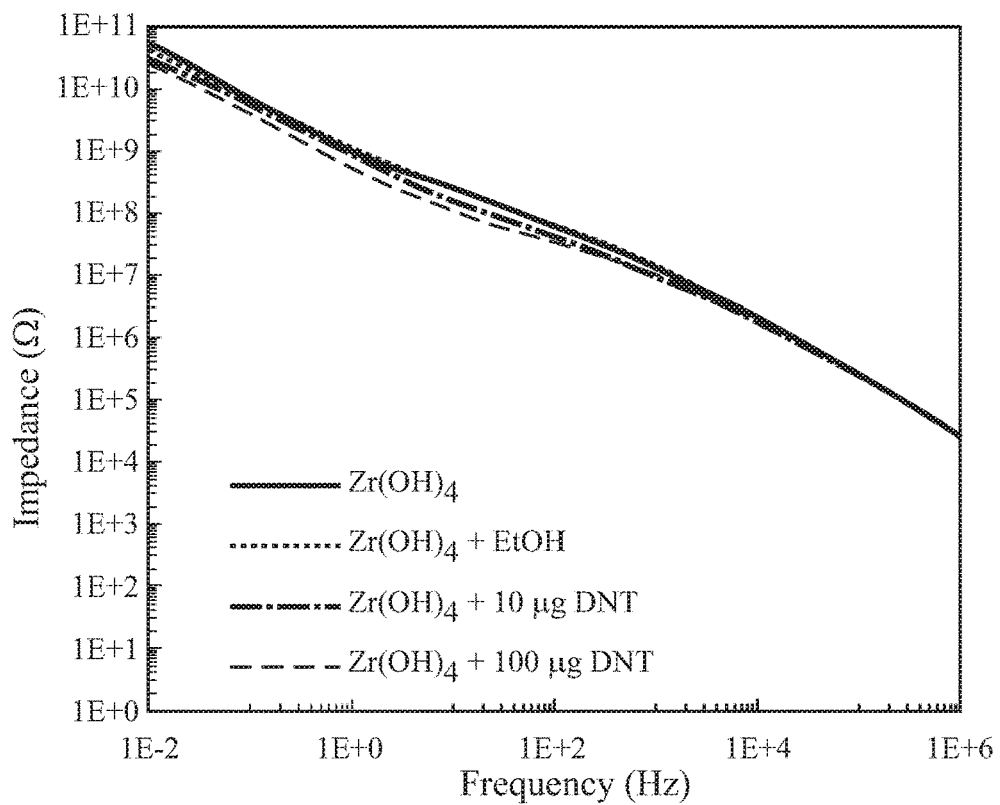
FIG. 4A illustrates changes in impedance by binding of 2,6-DNT by the detection agent Zr(OH)$_4$.
Figure 4B:
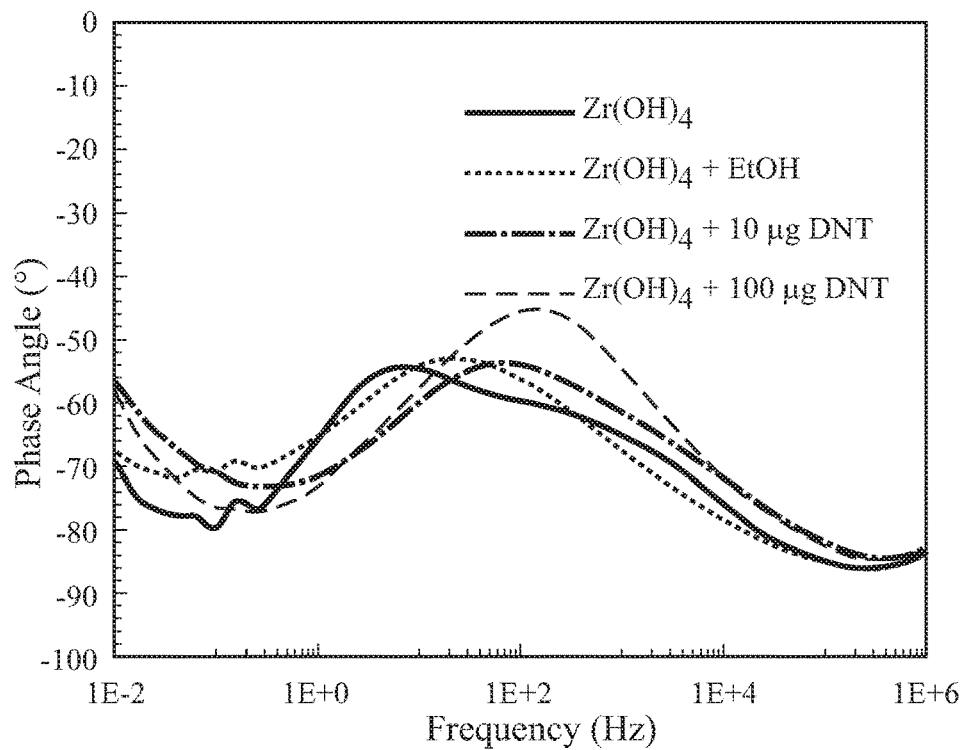
FIG. 4B illustrates changes in the resistive behavior, as reflected in the phase angle due to the binding of NO$_2$ by the detection agent Zr(OH)$_4$.
Figure 4C:
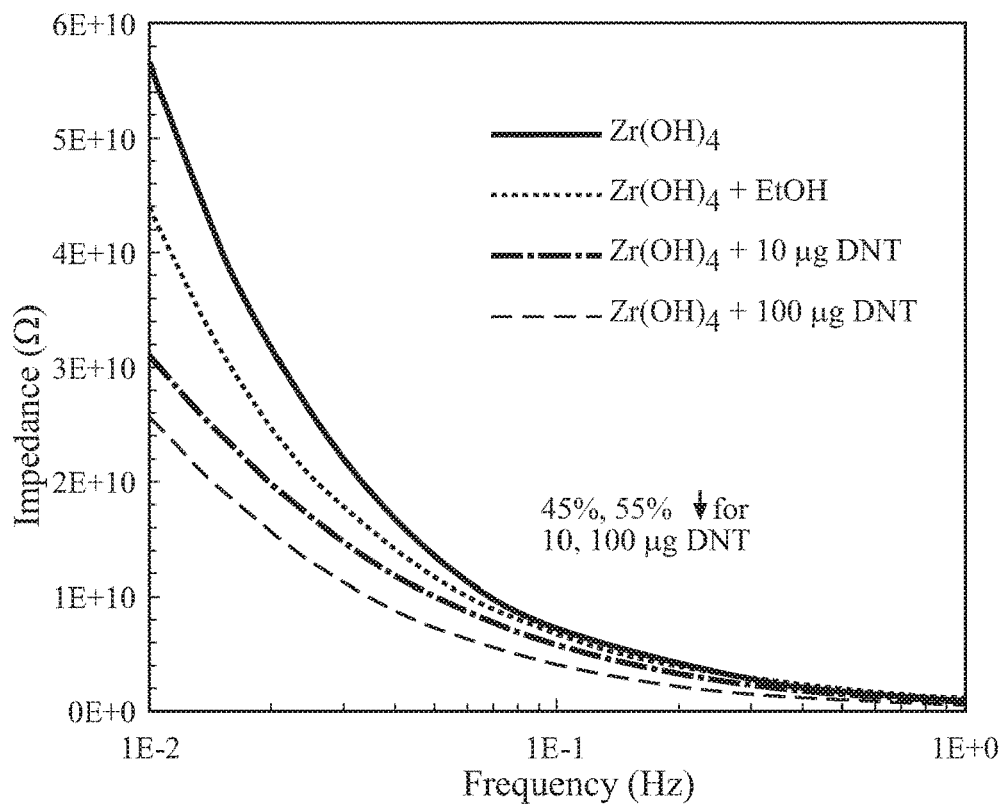
FIG. 4C illustrates the impedance range of FIG. 4A within the narrower frequency band of 0.01 Hz to 1 Hz.
Figure 4D:
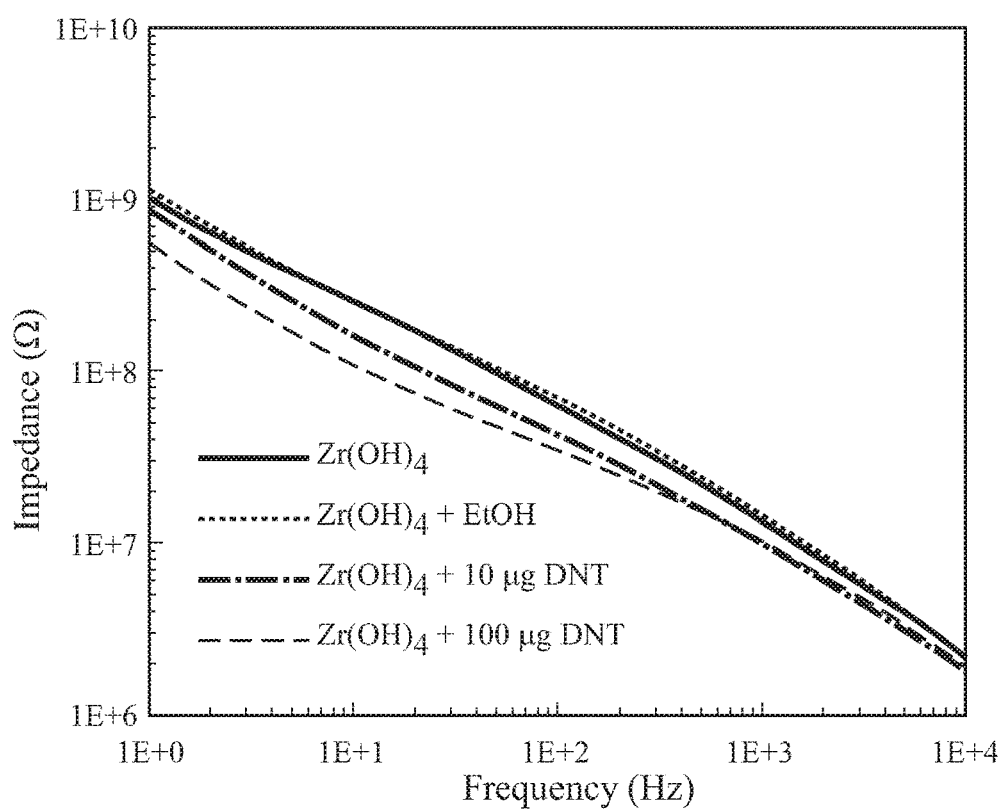
FIG. 4D illustrates the impedance range of FIG. 4A within the narrower frequency band 1 Hz to 10000 Hz.
Figure 5A:
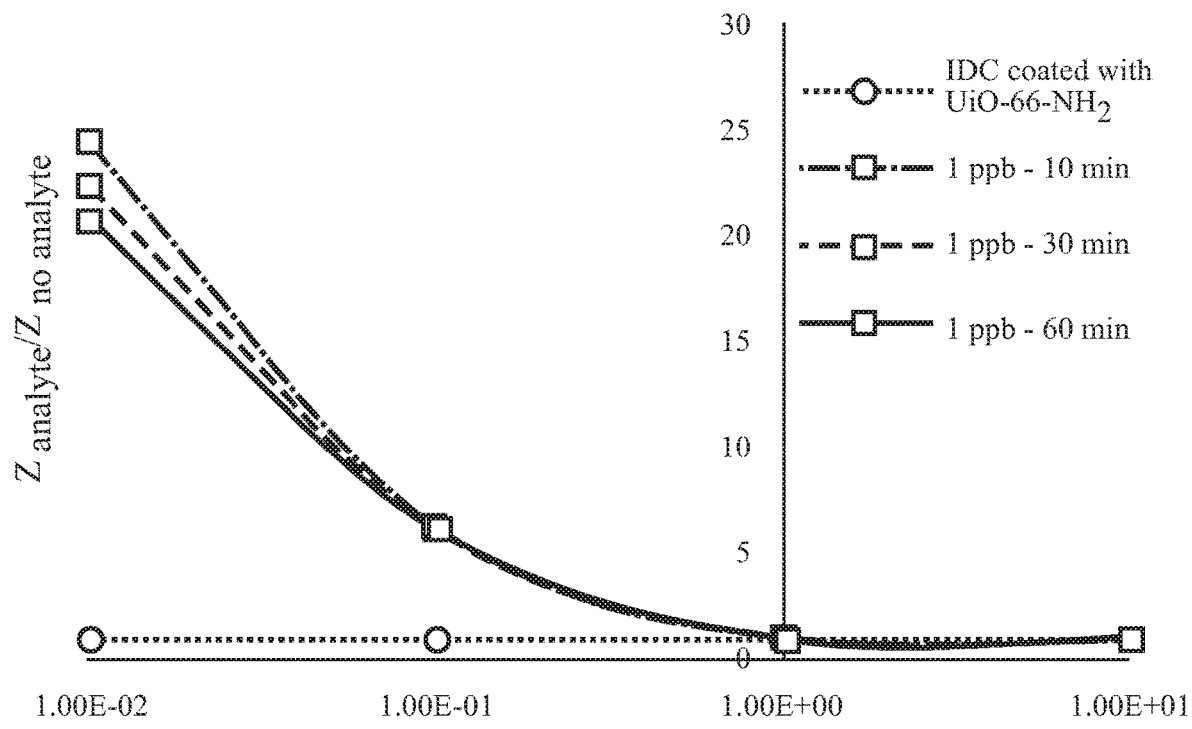
FIGS. 5A-5D illustrate the frequency dependence of the absorption of 2,6-DNT by UiO-66-NH$_2$ as detected on the surface of an interdigitated capacitor at a concentration of (A) 1 pph, (B) 10 pph, (C) 100 ppb, and (D) 746 ppb.
Figure 5B:
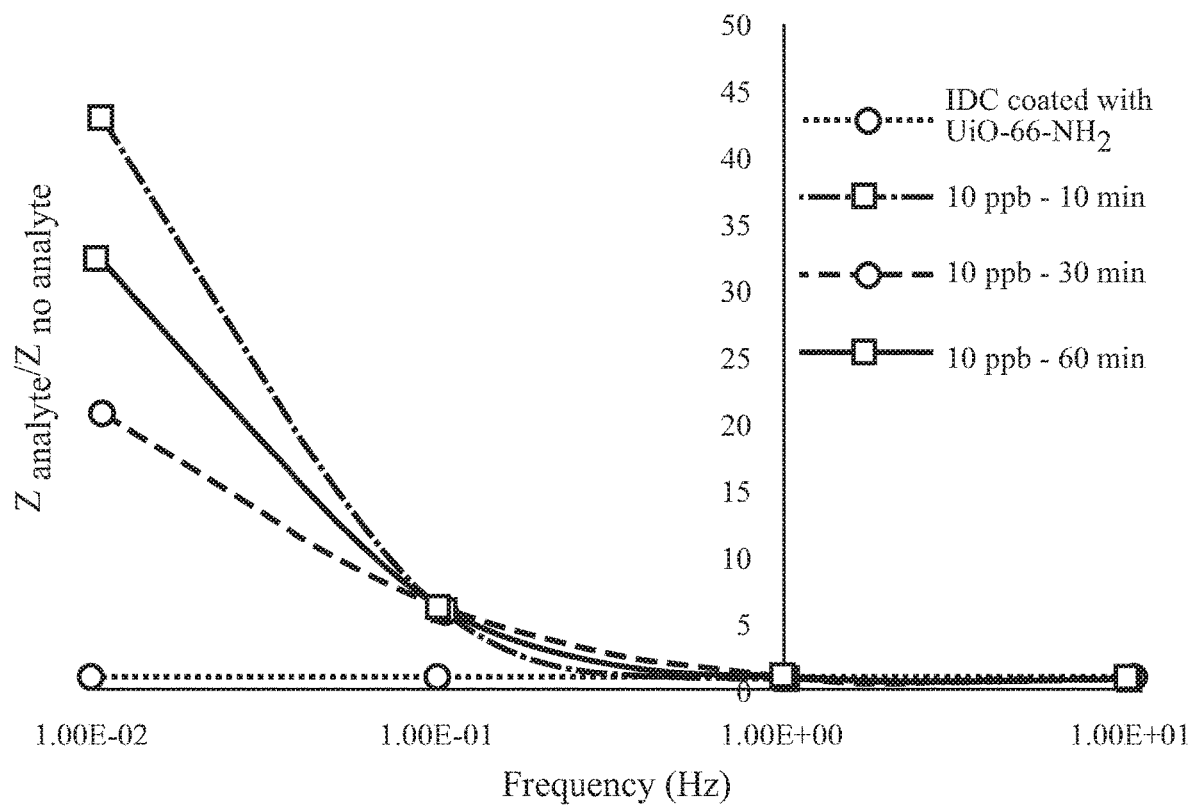
Figure 5C:
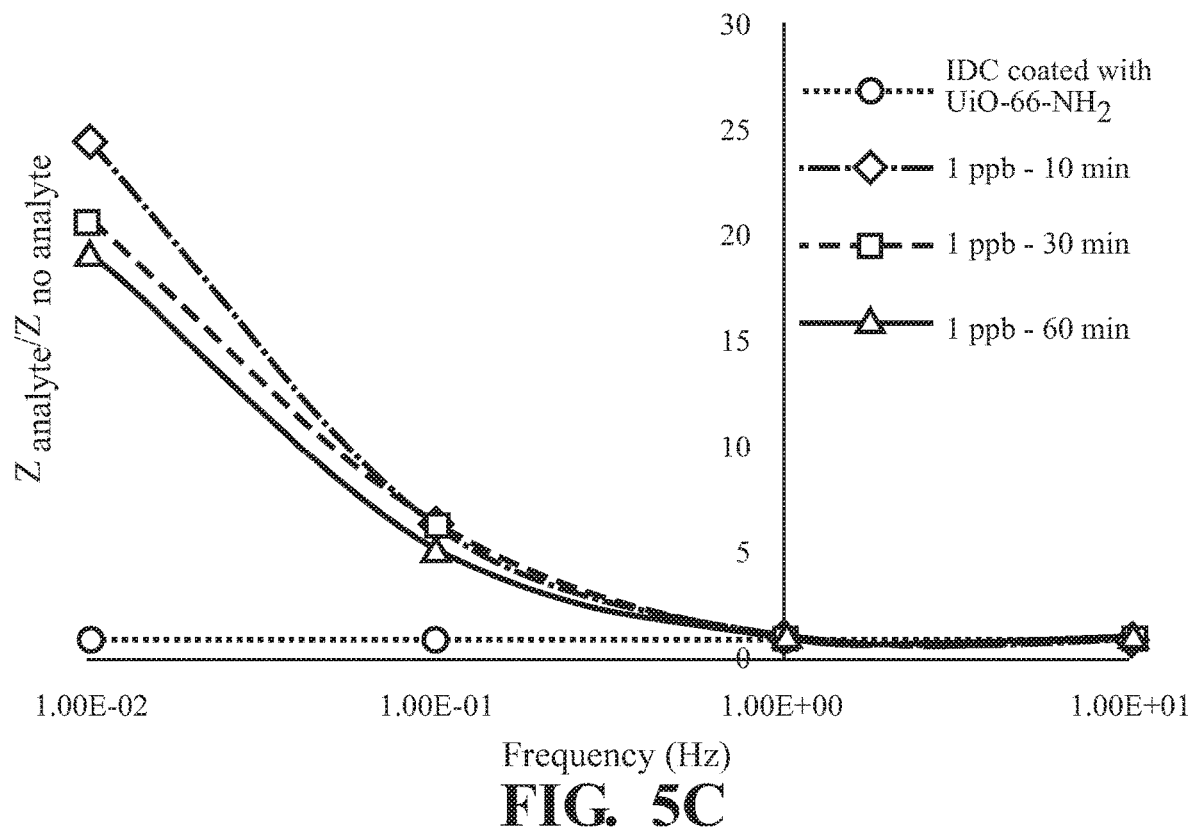
Figure 5D:
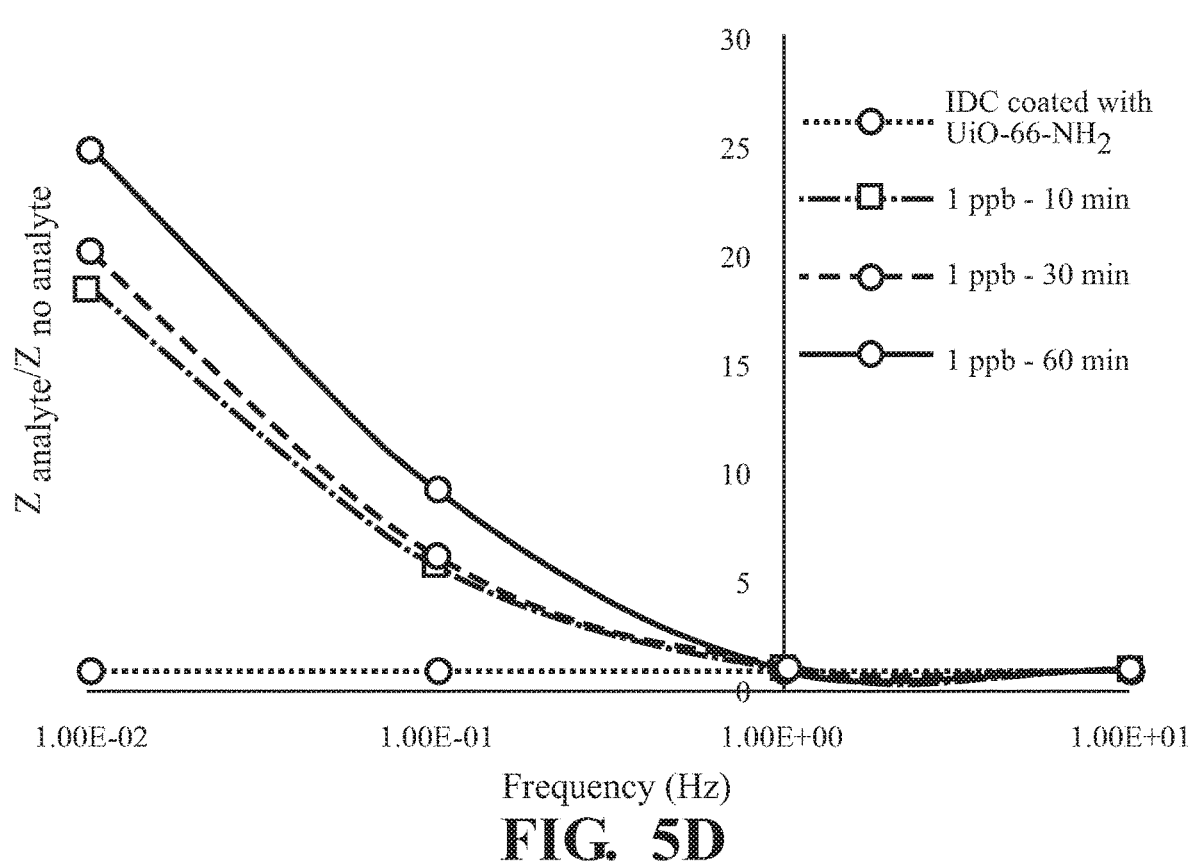
Figure 6A:
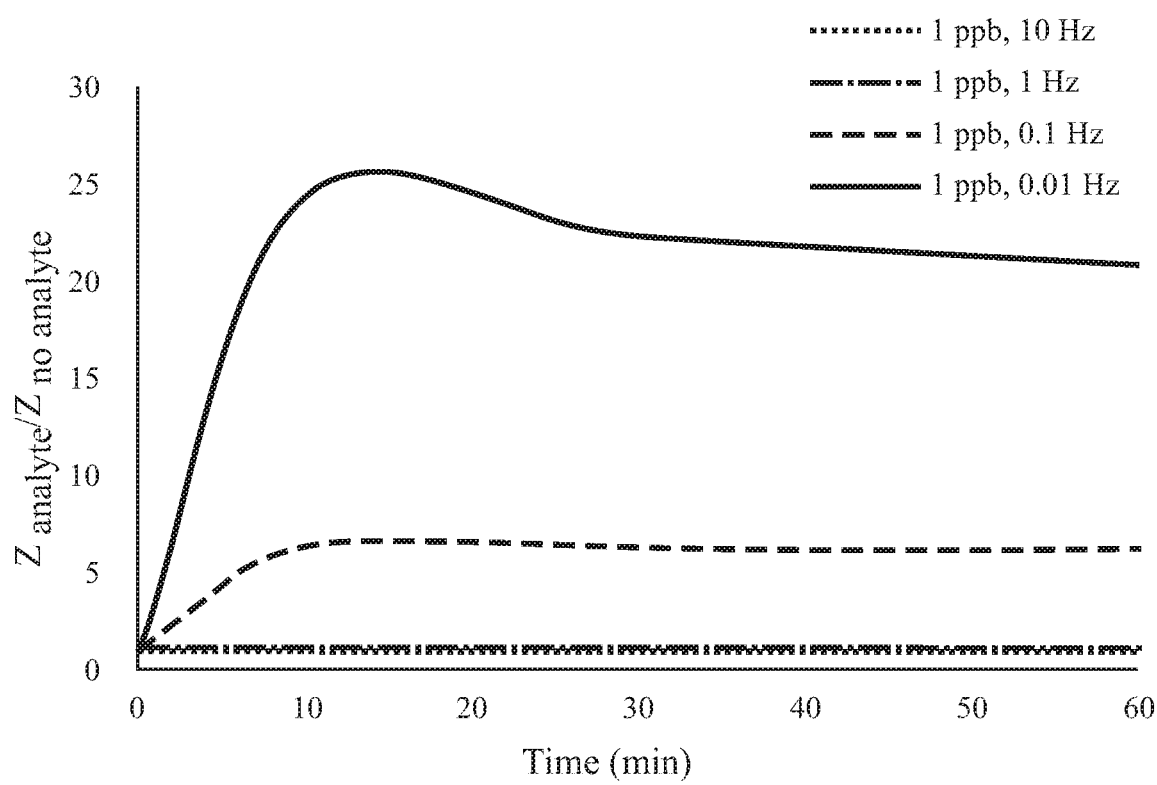
FIGS. 6A-6D illustrate the effect of exposure time to 2,6-DNT to a UiO-66-NH$_2$ as detected on the surface of an interdigitated capacitor with detection at varying frequencies at a concentration of (A) 1 pph, (B) 10 ppb, (C) 100 ppb, and (D) 746 ppb.
Figure 6B:
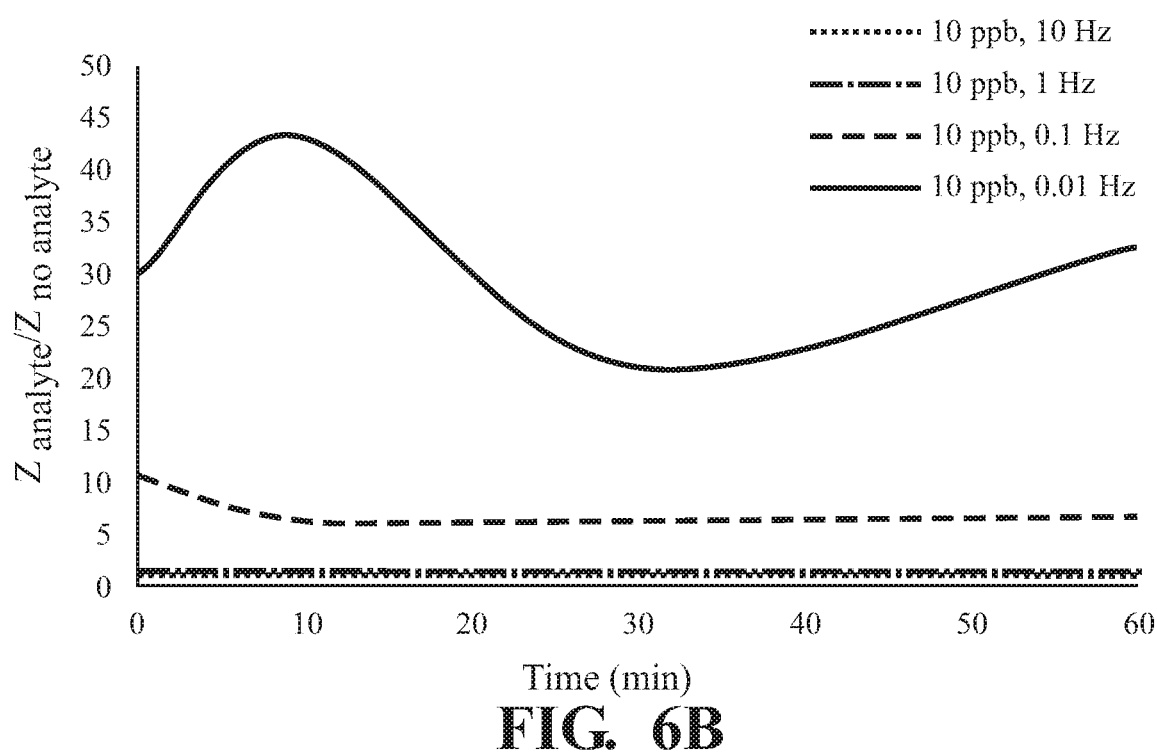
Figure 6C:
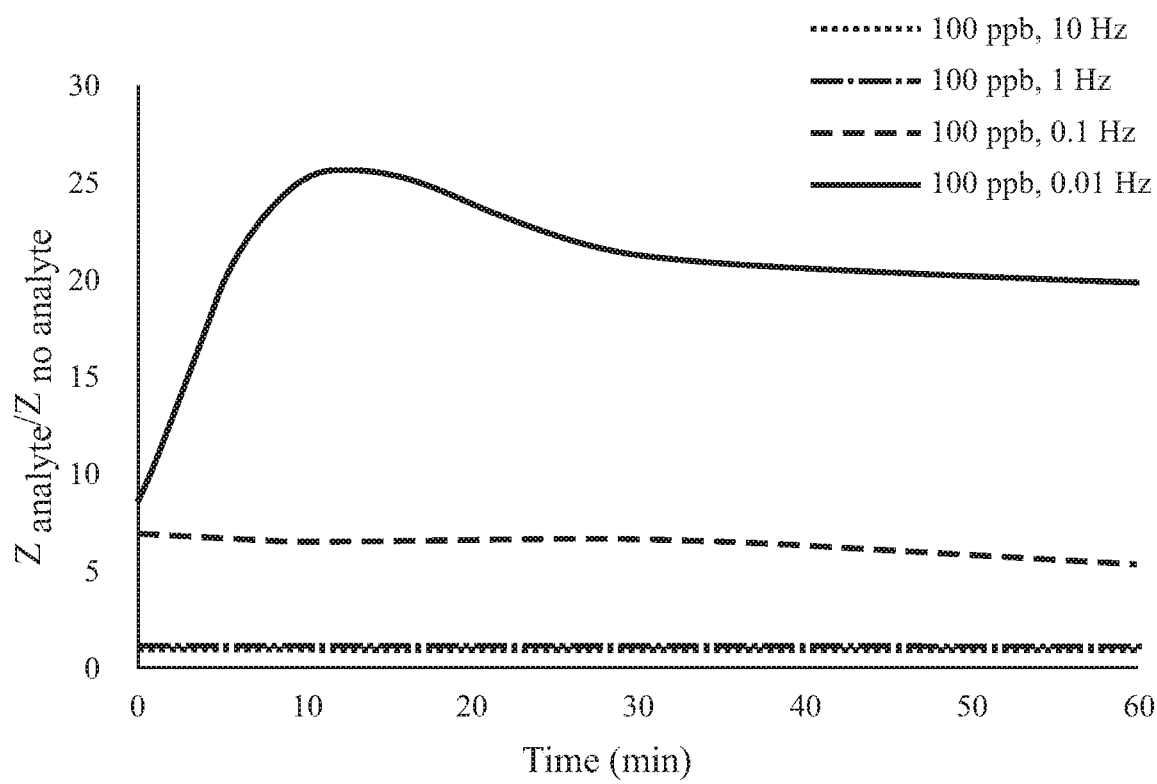
Figure 6D:
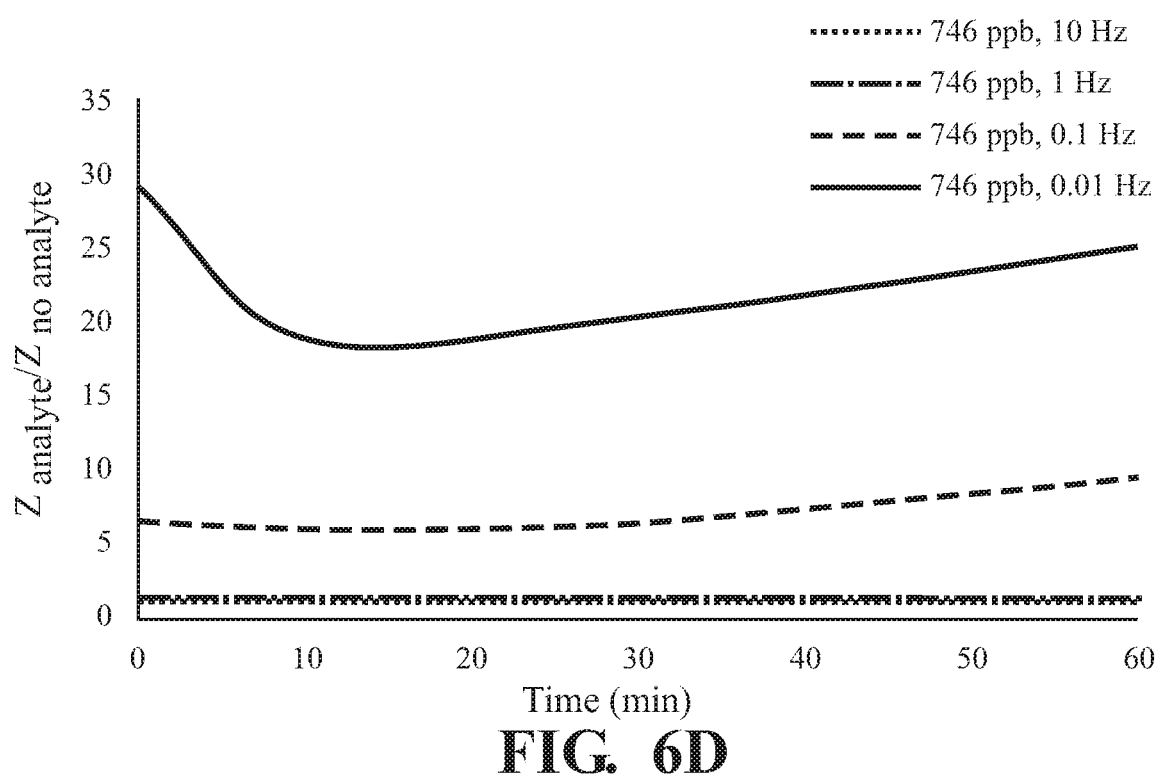

Zr(OH)$_4$ was prepared as in Example 3 and subjected to various amounts of 2,6-DNT as per Example 2. The interaction of the Zr(OH)$_4$ detection agent with the chemical was analyzed using a parallel plate capacitor at an applied voltage of 100 mV. The resulting magnitude of impedance and phase angle as a function of frequency for Zr(OH)$_4$ exposed to ethanol and trace quantities of 2,6-dinitrotoluene are illustrated in FIGS. 4A and 4B respectively. FIGS. 4C and 4D illustrate impedance changes as illustrated in FIG. 4A magnifying particular regions of the trace. Since the explosive simulant was mixed with ethanol, the solvent was evaluated to confirm minor changes in the electrical response. From the 10 µg and 100 µg of 2,4-dinitrotoluene exposures, a 45% and 55% change in the magnitude of |Z| in the low frequency regime was observed, confirming the utility of Zr(OH)$_4$ as an excellent material for sensing toxic chemicals by EIR. Changes at the higher frequency regime appear to be negligible as the changes are not significant.

Example 5

Detection of Chemicals Using Interdigitated Capacitors

Composites including the material of interest, such as a polymer (e.g. PEA or PVP) and a metal oxide or metal organic framework (UiO-66-NH$_2$ for sensing 2,6-DNT), etc. in a 1 to 10 ratio, were fabricated, on the surface of an IDC using an ultra-sonic spray deposition technique for uniform film thickness. Film thicknesses of the composite ranged on the scale of nanometers to micrometers. Cu or brass was used as the metal in the working electrodes for the IDC design. The IDCs with the film coatings were then annealed in air at 120° C. for a 2-3 hours followed by placing in a desiccator until execution of AC impedance measurements.

All AC impedance measurements were collected using a Solartron 1260 impedance system equipped with a 1296 dielectric interface. The frequency was swept from 1 MHz to 0.01 Hz at such applied voltages as 10, 100, and 1000 mV. As another set of experiments, AC impedance measurements were collected while holding the frequency at 10, 1, 0.1, or 0.01 Hz with an applied voltage as 100 mV. Toothless alligator clips connected to 50Ω BNC cables were used to connect to the IDC. A baseline impedance measurement in air was collected of the IDC coated with the film coating before analyte exposure. The detection agent was exposed to chemical 2,6-DNT in both liquid and vapor exposures. For liquid exposure, such concentrations as 1, 10, 100, and 1000 ppb of the chemical mixed with a solvent such as MeOH were made, The chemical solutions were drop casted sin the IDC coated with the film, and set to dry for 15 min for full evaporation of liquid before impedance measurements were collected. For vapor exposures, the IDC coated with the film were placed in a closed form atmosphere testing chamber. In-situ impedance measurements with the analyte mixed with dry air (less than 5% humidity) were carried out at 1, 10, 100, and 746 ppb concentrations for set timed periods, i.e. 10, 30, and 60 minutes as well as overnight exposures. Overall, the finger-print response to the analyte showed sensitivity in the DC range (10 to 0.01 Hz).

Figure 7A:
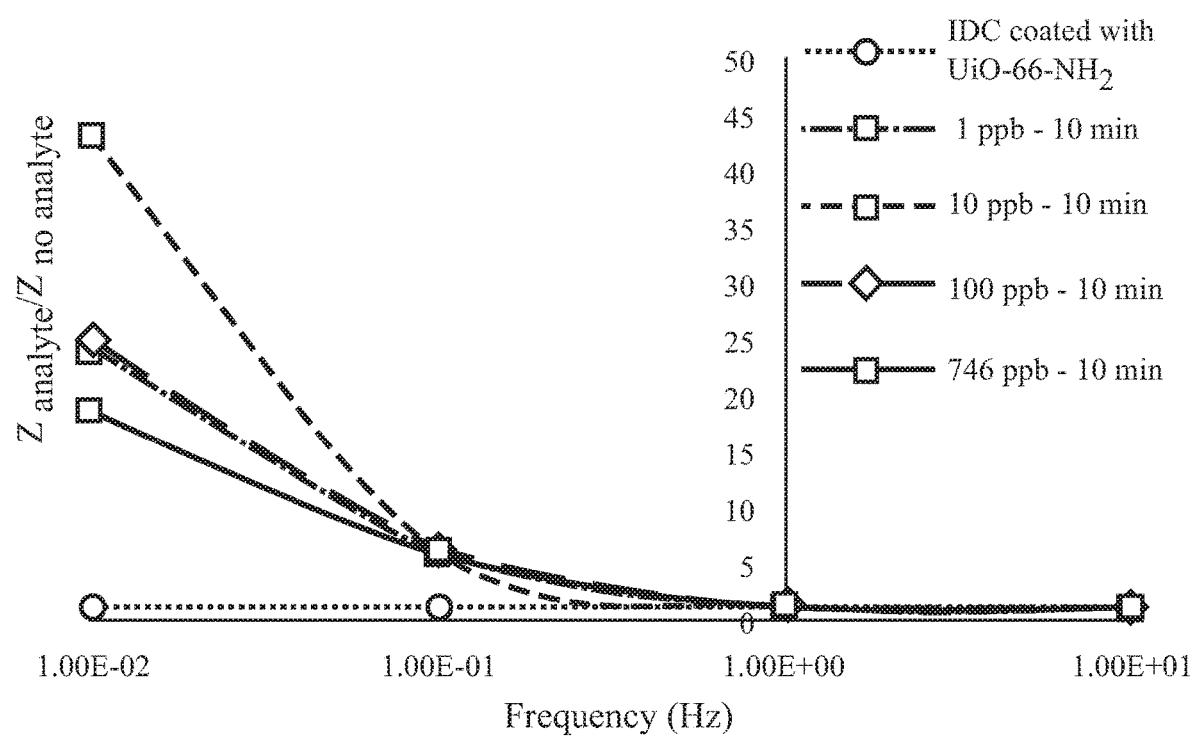
FIGS. 7A-7C illustrates concentration dependence at various absorption times of (A) 10 min, (B) 30 min, and (C) 60 min.
Figure 7B:
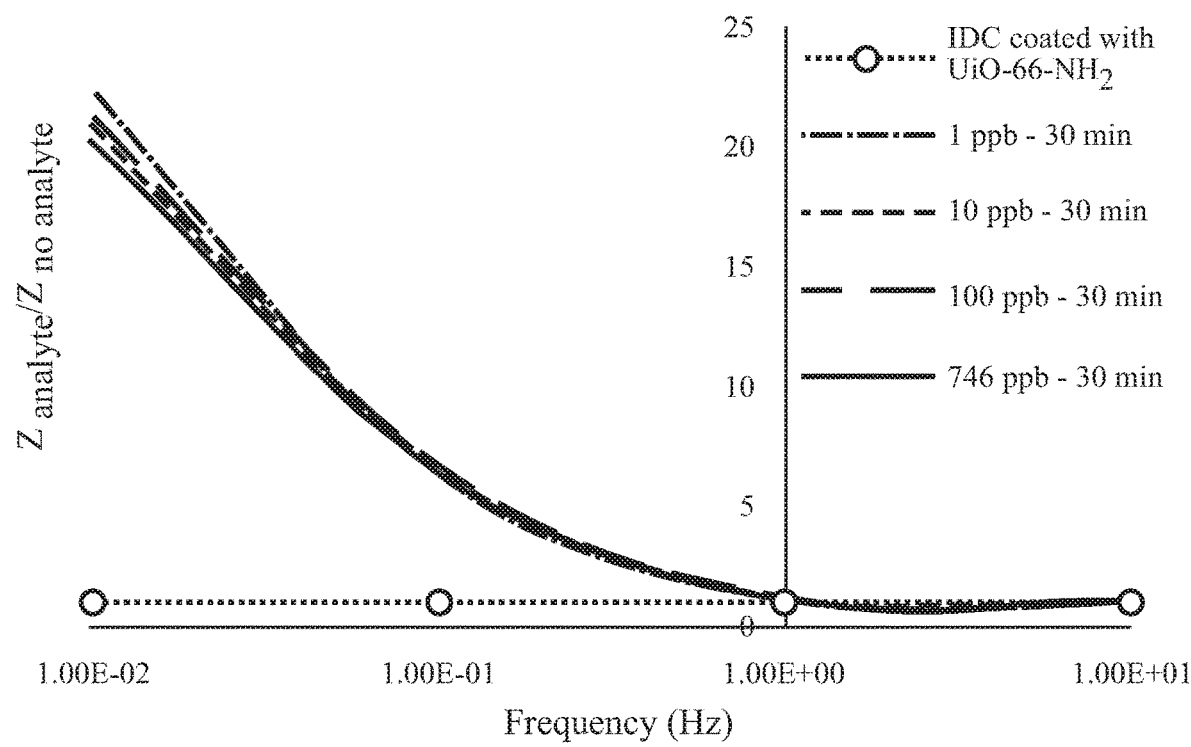
Figure 7C:
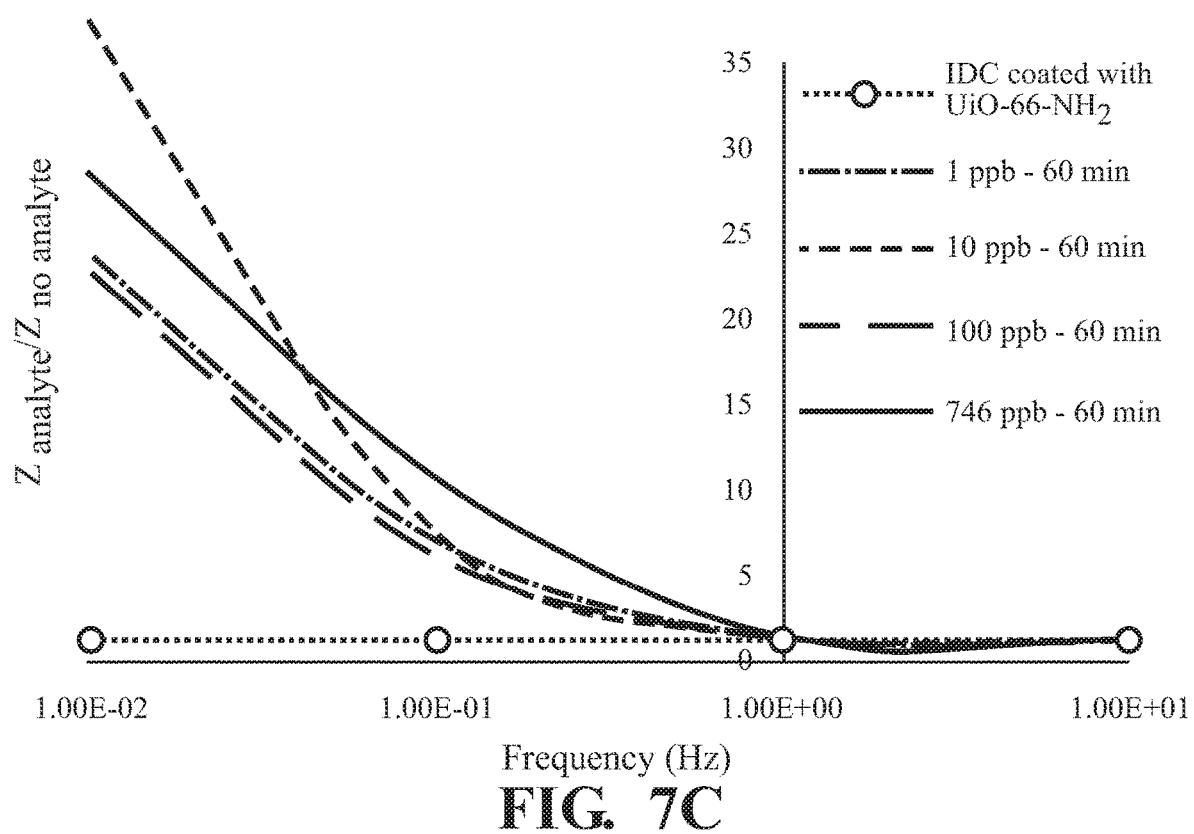

As illustrated in FIG. 5, absorption of 2,6-DNT is observed in at all concentrations tested with a frequency dependent response and the greatest difference in Z observed at 0.01 Hz for all incubation times tested,. The effect of exposure time on response of Z at various concentrations of 2,6-DNT are illustrated in FIGS. 6A-D demonstrating a finger-print, non-monotonic response of Z. Similar results are illustrated at each of the tested absorption times in FIG. 7. Overall, a fingerprint recognition is observed.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

REFERENCE LIST

1 Hill, H. H. & Simpson, G. Capabilities and limitations of ion mobility spectrometry for field screening applications. *Field Analytical Chemistry & Technology* 1, 119-134 (1997).
2 Goltz, M. N., Kim, D. S. & Racz, L. Using Nanotechnology to Detect Nerve Agents. *AIR UNIV MAXWELL AFB AL AIR FORCE RESEARCH INST* (2011).
3 Peterson, G. W., Karwacki, C. Feaver, W. B. & Rossin, J. A. Zirconium Hydroxide as a Reactive Substrate for the Removal of Sulfur Dioxide. *Industrial & Engineering Chemistry Research* 48, 1694-1698, doi:10.1021/ie801403h (2009).
4 Mogilevsky, G., Karwacki, C. J., Peterson, G. W. & Wagner, G. W. Surface hydroxyl concentration on Zr(OH) (4) quantified by H-1 MAS NMR. *Chemical Physics Letters* 511, 384-388, doi:10.1016/j.cplett.2011.06.072 (2011).
5 Peterson, G. W., Rossin, S. A., Karwacki, C. J. & Glover, T. G. Surface Chemistry and Morphology of Zirconia Polymorphs and the Influence on Sulfur Dioxide Removal. *Journal of Physical Chemistry C* 115, 9644-9650, doi:10.1021/jp201173x (2011).
6 Singh, et al. Sulfur dioxide and nitrogen dioxide adsorption on zinc oxide and zirconium hydroxide nanoparticles and the effect on photoluminescence. *Applied Surface Science* 258, 5778-5785, doi:10.1016/j.apsusc.2012.02.093 (2012).
7 Wafters, E. J., Sengupta, S. K., Peterson, G. W. & Whitten, J. E. Photoluminescence of zirconium hydroxide: Origin of a chemisorption-induced 'red-stretch'. *Chem. Phys. Lett.* 592, 297-301, doi: 10.1016/j.cplett.2013.12.035 (2014).
8 Peterson, G. W., DeCoste, J. B., Fatollahi-Fard, F. & Britt, D. K. Engineering UiO-66-NH2 for Toxic Gas Removal. *Industrial & Engineering Chemistry Research* 53, 701-707, doi:10.1021/ie403366d (2014).
9 DeCoste, J. B., Browe, M. A., Wagner, G. W., Rossin, J. A. & Peterson, G. W. Removal of chlorine gas by an amine functionalized metal-organic framework via electrophilic aromatic substitution. *Chemical Communications* 51, 12474-12477, doi:10.1039/C5CC03780H (2015).
10 Peterson, G. W., Mahle, J. J., DeCoste, J. B., Gordon, W. O. & Rossin, J. A. Extraordinary $NO_2$ Removal by the Metal-Organic Framework UiO-66-NH2. *Angew. Chem., Int. Ed.*, Ahead of Print, doi:10.1002/anie.201601782 (2016).

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

We claim:

1. A process for detecting the a presence of a chemical, comprising:
contacting a chemical with a surface comprising one or more detection agents, the one or more detection agents comprising a metal organic framework, metal oxide, or both, the surface intermediate to and electrically connected to a pair of electrodes; and
detecting the chemical through electrical impedance spectroscopy by subjecting the surface to an alternating current at a range of frequencies, the range from $10^{-2}$ to $10^6$ Hertz, and measuring changes in impedance magnitude and/or phase angle over that range of frequencies.

2. The process of claim 1, wherein the surface further comprises a polymer, an absorbent, or combination thereof.

3. The process of claim 1, wherein said detecting the chemical through electrical impedance spectroscopy further comprises subjecting the surface to an applied voltage of 10 milliVolts to 10 Volts.

4. The process of claim 1, wherein said detecting the chemical through electrical impedance spectroscopy further comprises subjecting the surface to a direct current.

5. The process of claim 1, wherein the metal organic framework or metal oxide is a porous media.

6. The process claim 1, wherein the chemical is a toxic chemical or explosive chemical.

7. The process of claim 1, wherein the metal organic framework comprises at least one pendant group in the framework, the at least one pendant group comprising an amine, nitro, or halide.

8. The process of claim 7, wherein the metal is selected from the group consisting of: Al; Si; Cr; Fe; Co; Ni; Cu; Zn; Hf; Mn; Ti; V; Zr; Ca; Mg; and the lanthanides.

9. The process of claim 1, wherein the metal organic framework is a UiO metal organic framework.

10. The process of claim 1, wherein the metal organic framework is selected from the group consisting of NU1000, UiO-66, UiO-66-NH2, UiO-67, $Zn_2(bpdc)_2(bpee)$, PCN-250, MIL-53-$NH_2$, MIL-125-$NH_2$, ZIF-8, PCN-250, MOF-74 (M-DOBDC), and PCN-222.

11. The process of claim 1, wherein the surface comprises an interdigitated capacitor that is reusable after chemical exposure.

12. The process of claim 11, wherein the changes in impedance magnitude and/or phase angle after the interdigitated capacitor has been exposed to a chemical are reversible following exposure to air for 3 days.

13. The process of claim 1, wherein the one or more detection agents comprise a metal oxyhydroxide.

14. The process of claim 13, wherein the metal oxyhydroxide comprises a transition metal or cation.

15. The process of claim 13, wherein the metal oxyhydroxide comprises a metal selected from the group consisting of: Al; Si; Cr; Fe; Co; Ni; Cu; Zn; Hf; Mn; Ti; V; Zr; Ca; Mg; and the lanthanides.

16. The process of claim 1, wherein the surface comprises a polymer exhibiting dielectric properties.

17. The process of claim 16, wherein the polymer comprises polyvinylidene fluoride.

18. The process of claim 1, wherein the one or more detection agents comprise zirconium hydroxide, $Zr(OH)_4$.

19. A process for detecting a presence of a chemical, comprising:
adsorbing a toxic chemical or an explosive chemical to a dielectric surface comprising one or more detection agents comprising a metal organic framework, a metal oxide/hydroxide, or combination thereof; and
detecting the chemical through electrical impedance spectroscopy by subjecting the surface to an alternating current at a range of frequencies, the range from $10^{-2}$ to $10^6$ Hertz, and measuring changes in impedance magnitude and/or phase angle over that range of frequencies.

20. The process of claim 19, wherein the one or more detection agents comprise a metal organic framework selected from the group consisting of NU1000, UiO-66, UiO-66-NH2, UiO-67, $Zn_2(bpdc)_2(bpee)$, PCN-250, MIL-53-$NH_2$, MIL-125-$NH_2$, ZIF-8, PCN-250, MOF-74 (M-DOBDC), and PCN-222; or
wherein the one or more detection agents comprise: zirconium oxyhydroxide, iron oxide, or any transition metal oxide/hydroxide.

21. The process of claim 19, wherein the toxic chemical comprises nitrogen dioxide, sulfur dioxide, chlorine, ammonia, and organophosphates.

22. The process of claim 19, wherein the explosive chemical comprises ammonium nitrate, cyclotrimethylenetrinitramine, pentaerythritol tetranitrate, octogen trinitrotoluene, 2,4-dinitrotoluene, or 2,6-dinitrotoluene.

* * * * *